United States Patent [19]

Young et al.

[11] Patent Number: 4,795,440
[45] Date of Patent: Jan. 3, 1989

[54] LOW-VOLUME NON-BUBBLE COLLECTING PRESSURE DOME

[75] Inventors: Joe W. Young, Laguna Hills; Michael V. North, Garden Grove; Kenneth W. Rake, Laguna Niguel, all of Calif.

[73] Assignee: Baxter International Inc., Deerfield, Ill.

[21] Appl. No.: 17,790

[22] Filed: Feb. 24, 1987

[51] Int. Cl.$^4$ .......................... A61M 5/00; G01L 7/08
[52] U.S. Cl. .................................. 604/122; 604/118; 73/730; 128/675
[58] Field of Search ............... 604/118, 121, 122, 123, 604/125; 73/715, 730; 128/675

[56] References Cited

U.S. PATENT DOCUMENTS

| | | | |
|---|---|---|---|
| 2,629,399 | 2/1953 | Kulick | 137/525 |
| 2,841,984 | 7/1958 | Green | 73/395 |
| 3,120,759 | 2/1964 | Pochapsky | 73/407 |
| 3,468,308 | 9/1969 | Bierman | 604/118 X |
| 3,713,341 | 1/1973 | Madsen et al. | 73/715 |
| 3,939,758 | 2/1976 | Faisandier | 73/406 X |
| 4,034,754 | 7/1977 | Virag | 604/122 X |
| 4,398,542 | 8/1983 | Cunningham et al. | 128/675 |
| 4,592,747 | 6/1986 | Pool | 73/715 X |

FOREIGN PATENT DOCUMENTS

| | | |
|---|---|---|
| 888933 | 7/1953 | Fed. Rep. of Germany . |
| 902723 | 2/1982 | U.S.S.R. . |

*Primary Examiner*—Dalton L. Truluck
*Attorney, Agent, or Firm*—Debra E. Dahl; Richard L. Myers; Gordon L. Peterson

[57] ABSTRACT

A pressure sensor comprising a main body having an inlet connectable to a source of liquid under pressure, an outlet, a passage extending through the main body from the inlet to the outlet and a surface outside of the passage. A flexible diaphragm confronts the surface and is coupled to the main body to at least partially define a sensing chamber. The main body has a port extending from the passage to the sensing chamber to provide communication between liquid under pressure in the passage and the sensing chamber. The port has a transverse cross section with at least one dimension which is no greater than about 0.060 inch.

14 Claims, 2 Drawing Sheets

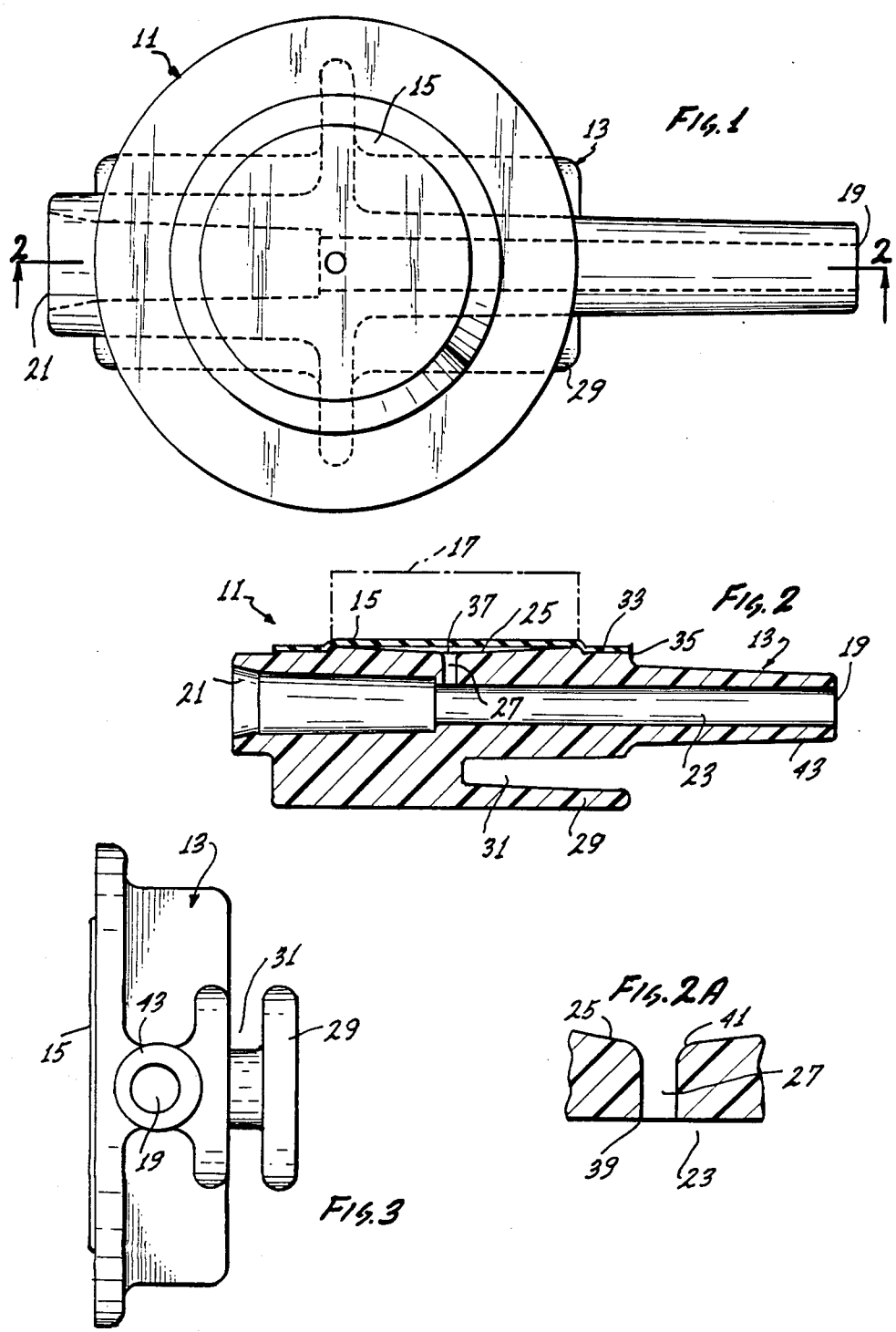

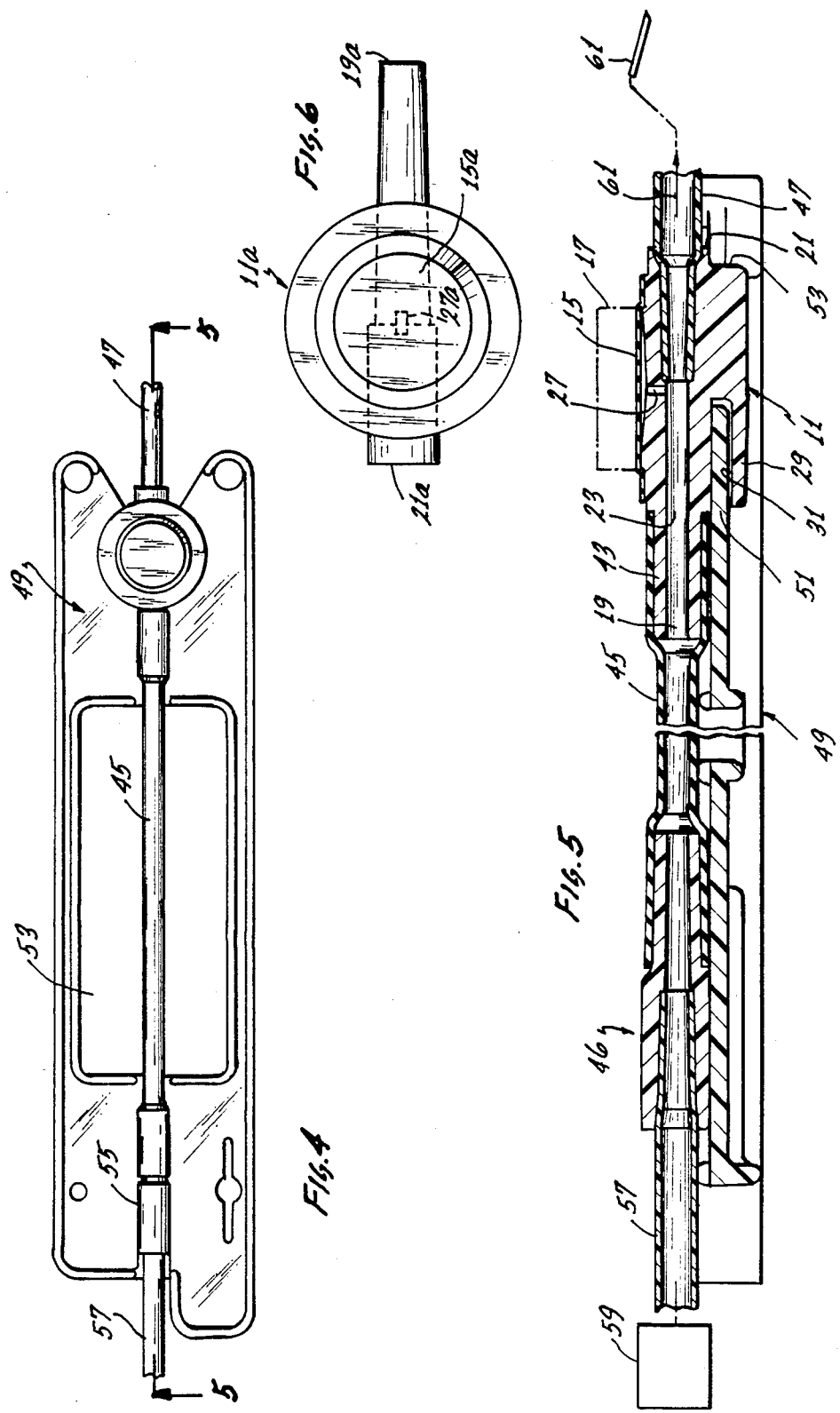

LOW-VOLUME NON-BUBBLE COLLECTING PRESSURE DOME

BACKGROUND OF THE INVENTION

Various parenteral liquids are administered to a patient under a positive pressure through an administration set. The positive pressure may be generated by gravity flow or by an appropriate pump. It is often necessary or desirable to monitor the pressure under which the fluids are delivered to the patient. This can be accomplished, for example, with a diaphragm or membrane type pressure sensor and a pressure transducer.

One problem with the sensing of pressure in an administration set is that the pressure sensor should not be allowed to trap any gas or bubbles that may exist in the liquid. If bubbles were trapped and, subsequently released and infused into the cardiovascular system of the patient, the results could be fatal to the patient.

One technique for pressure monitoring is to place a diaphragm over the top of an elongated channel through which the liquid flows and devices of this type are shown, for example, in German Pat. No. 888,933 and Cunningham et al U.S. Pat. No. 4,398,542. According to Cunningham et al, this approach does not trap air in the pressure sensor.

Another approach, which is structurally simpler, is to simply tap into the conduit of the administration set using a Tee to couple the pressure sensor to the conduit. However, this approach makes it difficult to purge air from the system and creates a likelihood of air entrapment in the Tee connection or in the pressure sensor.

SUMMARY OF THE INVENTION

This invention employs a pressure sensor which is more akin to the Tee connection approach, but does so in a manner that facilitates purging of air from the system and which minimizes the likelihood of air or bubble entrapment in the pressure sensor. With this invention, a port leads from a flow passage in a main body to a pressure sensing chamber. The port is constructed in a way so as to substantially prevent the passage of bubbles into the sensing chamber.

In a preferred construction, the pressure sensor includes a main body having an inlet connectable to a source of liquid under pressure, an outlet, and a flow passage extending through the main body from the inlet to the outlet so that liquid can flow through the passage. Means including a diaphragm coupled to the main body define a sensing chamber. The pressure sensor also includes means defining a port within the main body which extends from the passage to the sensing chamber to provide communication between the liquid under pressure in the passage and the sensing chamber.

The invention employs a number of features substantially preventing the sensing chamber from serving as a bubble trap. This is accomplished primarily by limiting at least one dimension of the transverse cross-section of the port to a dimension which enables the surface tension to substantially exclude bubbles for the viscosity and pressure of interest. For parenteral liquids, this dimension is preferably no more than about 0.060 inch. When so limited, the surface tension substantially excludes bubbles from passing through the port for the liquid viscosity levels and pressures of interest in the parenteral administration of liquids to a patient. Parenteral fluids normally have a viscosity no less than the viscosity of water and are delivered at pressures no greater than about 22 psi. Preferably the port has a lesser cross-sectional area than the cross-sectional area of the passage. The port may be circular, rectangular, irregular or of virtually any configuration provided that the dimensional parameters of the invention are followed.

The pressure sensing chamber senses only static pressure, and so theoretically, the controlled dimension of the port does not have a minimum. However, to facilitate manufacture, minimize the danger of plugging and to eliminate unfavorable time delays in sensing pressure changes, the controlled dimension of the port is preferably no less than 0.020 inch. Furthermore, if the port is to be formed in a molding operation, it is preferred that the controlled dimension be no less than 0.030 inch.

To further minimize the likelihood of the transmission of bubbles from the flow passage through the port to the sensing chamber, the port preferably has sharp edges with essentially no radius at the location where the controlled dimension of the port exists. Preferably, the sharp edges are at the juncture of the port with the flow passage.

To facilitate priming, the length of the port should be minimized. The length of the port preferably does not exceed 2.5 times the controlled dimension of the port or 0.150 inch maximum. By limiting the length of the port, the height of the column of air that must be initially purged from the pressure sensor is reduced.

The pressure sensing chamber is also preferably of minimum volume and may have a volume of 0 when there is no pressure differential across the diaphragm. However, to facilitate purging, the sensing chamber preferably has a conical surface into which the diaphragm can be deflected with thumb pressure to eject air from the pressure sensor during purging by a reciprocating manual pumping action. Thus, the conical surface facilitates air elimination from the system during purging.

Prior to purging, there is air in the administration set and in the sensing chamber. To facilitate removal of the air from the sensing chamber, the port at the location where it meets the conical surface or other corresponding surface preferably has a radiused edge.

The main body is preferably integrally molded from a suitable plastic material and includes a surface outside of the passage which the flexible diaphragm confronts to define the sensing chamber. The main body can advantageously be mounted on external supporting structure, such as a cassette frame. To accomplish this, the main body preferably has a lug integral therewith partly defining a slot for use in coupling the main body to such external supporting structure.

The invention, together with additional features and advantages thereof may best be understood by reference to the following description taken in connection with the accompanying illustrative drawing.

BRIEF DESCRIPTION OF THE DRAWING

FIG. 1 is a top plan view of one form of pressure sensor constructed in accordance with the teachings of this invention.

FIG. 2 is a sectional view taken generally along line 2—2 of FIG. 1.

FIG. 2a is an enlarged fragmentary sectional view of the region of the main body adjacent the port.

FIG. 3 is an end elevational view of the pressure

FIG. 4 is a top plan view of the pressure sensor mounted on a cassette frame.

FIG. 5 is a sectional view taken generally along line 5—5 of FIG. 4 showing an administration set which includes the cassette frame.

FIG. 6 is a top plan view showing another embodiment of pressure sensor.

DESCRIPTION OF THE PREFERRED EMBODIMENT

FIGS. 1–3 show a pressure sensor 11 which comprises a main body 13 and a flexible diaphragm or membrane 15. The pressure sensor 11 is adapted to be used with a pressure transducer 17, which may be of conventional construction and which is shown in broken lines in FIG. 2.

Although the main body 13 can be constructed of metal, it is preferably integrally molded from a suitable plastic material, such as PVC. The main body 13 includes an inlet 19, an outlet 21 and a generally cylindrical flow passage 23 extending linearly between the inlet and the outlet. The inlet 19 is adapted for connection to a source of parenteral liquid under pressure. The main body 13 has a conical surface 25 and a port 27 leading from the passage 23 to the apex of the conical surface 25. The main body 13 has a lug 29 which forms one side of a slot 31 for use in mounting the pressure sensor 11 as described hereinbelow with reference to FIGS. 4 and 5.

The main body 13 has an annular flat surface 33 surrounding a shoulder 35 on its exterior. The diaphragm 15, which is circular in the embodiment illustrated, has an annular peripheral zone ultrasonically bonded to the annular surface 33. The conical surface 25 cooperates with the diaphragm 15 to form a sensing chamber 37 of very small volume which communicates with the passage 23 via the port 27. Accordingly, the static pressure within the sensing chamber 37 is approximately equal to the static pressure within the passage 23. The static pressure of the liquid in the chamber 37 can deflect the diaphragm 15, and these deflections are sensed by the pressure transducer 17 in a conventional manner to provide an indication of the static pressure of the liquid under pressure within the passage 23.

Although the port 27 could pass through a separate member in addition to, or in lieu of, the main body 13, manufacture is facilitated if the port extends through the main body. Although the port 27 could be of various different configurations, in this embodiment, it is cylindrical.

To exclude bubbles or air from passing from the passage 23 through the port 27 into the sensing chamber 37, the port 27 has a diameter of no more than about 0.060 inch. The preferred minimum diameter of the port 27 may be 0.020 inch or 0.030 inch as discussed above. Although this diameter could exist at various locations along the length of the port, in this embodiment it exists at the juncture of the port 27 with the passage 23 and for substantially the full length of the port. To further tend to exclude air, the port 27 has a sharp circular edge 39 (FIG. 2a) with essentially no radius where it meets the passage 23.

The port 27 at the location where it meets the conical surface 25 has an annular radiused edge 41. Preferably, the radius is relatively long and may extend for all or a substantial portion of the length of the port 27, if so desired. The port 27 has an axial length or column height of no more than about 2.5 times its diameter, and in this embodiment, the length of the port is about 0.150 inch. The port 27 also has a lesser cross-sectional area than the cross-sectional area of the passage 23.

The inlet 19 is formed in a nipple 43 so that it can be inserted within one end of a flexible tube 45 (FIG. 5) of an administration set 46. The outlet 21 has an enlarged diameter so that an end portion of a flexible tube 47 may be inserted into it as shown in FIG. 5. Although the pressure sensor 11 can be caused to communicate with tubes carrying a fluid under pressure in various different ways, the pressure sensor is particularly adapted to be mounted on a frame 49 as shown in FIGS. 4 and 5. When so mounted, the slot 31 frictionally receives a tongue 51 of the frame.

Although the frame 49 can be of various different constructions, in this embodiment it has a central opening 53, and it carries at the end opposite the pressure sensor 11 a tubing coupling 55. The tubing coupling 55 joins the other end of the tube 45 to a tube 57 which extends to a source 9 of parenteral liquid.

The tube 45 is compressible and suitable for use in a peristaltic pump. The opening 53 provides a space in which the tubing 45 may be sequentially compressed in peristaltic pumping fashion by a peristaltic pump (not shown). This generates a pressure head for transmitting liquid from the source 59 of parenteral liquid through the pressure sensor 11, the tube 47 and a suitable device, such as an IV needle 61 to a patient. Accordingly, conduit means is provided for administering the parenteral liquid.

Prior to use, all of the components of the administration set including all of the tubes, the port 27, and the sensing chamber 37 contain air, and this air must be purged from the system. To do that, the attendant manually depresses the diaphragm 15 tightly against the conical surface 25 to expel the air from the sensing chamber 37. Then liquid from the source 59 is allowed to flow by gravity through the IV needle 61. By repeatedly depressing the diaphragm 25 with thumb pressure and then releasing it, liquid can be drawn through the port 27 into the sensing chamber 37 to thereby completely expel air from this portion of the system. The expulsion of air is facilitated by the radiused edge 41. Thus the port 27 makes it somewhat easier for a bubble to leave the sensing chamber than to enter it.

The sensing chamber 37 is not a flow-through chamber in that the port 27 effectively isolates the chamber from the liquid flowing in the passage 23. During use, there is essentially no flow through the port 27 to or from the sensing chamber 37. During operation the static pressure in the sensing chamber 37 is essentially the same as in the passage 23, and such pressure is monitored by the transducer 17. If air or bubbles are present in the liquid being pumped, it is highly unlikely that any bubble will pass through the port 27 into the sensing chamber 37 because of the surface tension being too great to allow the bubble to pass through the small diameter in the port 27. The sharp edge 39 also makes it more difficult for a bubble to travel from the passage 23 through the port 27 to the sensing chamber 37.

FIG. 6 shows a pressure sensor 11a that is identical to the pressure sensor 11, except that the port 27a is rectangular rather than cylindrical. Portions of the pressure sensor 11a corresponding to portions of the pressure sensor 11 are designated by corresponding reference numerals followed by the letter "a."

The port 27a has a long dimension 63 and a controlled or short dimension 65. The short dimension 65 is no more than 0.060 inch and preferably has a minimum in accordance with the parameters discussed above for the controlled dimension of the port. The long dimension 63 may, if desired, exceed 0.060 inch because, the short dimension will be controlling in preventing the passage of bubbles through the passage port 27a. The length of the port 27a preferably is no greater than about 2.5 times the short dimension 65.

Although exemplary embodiments of the invention have been shown and described, many changes, modifications and substitutions may be made by one having ordinary skill in the art without necessarily departing from the spirit and scope of this invention.

We claim:

1. A pressure sensor comprising:
   a main body having an inlet connectable to a source of liquid under pressure which is subject to having bubbles therein, an outlet and a passage extending through the main body from the inlet to the outlet so that liquid can flow through the passage;
   a flexible diaphragm coupled to the main body and confronting a conical surface for defining a low-volume surface sensing chamber on the main body;
   a port defined in the main body extending from said passage to said sensing chamber to provide communication between liquid under pressure in the passage and the sensing chamber; and
   said port having at the juncture of the port and the passage, a transverse cross-section with at least one dimension sufficiently small to enable surface tension to substantially exclude bubbles in the liquid flowing through the passage from passing through the port into the sensing chamber, said port having a sharp edge with essentially no radius at said juncture which further serves to exclude bubbles in the liquid from passing through the port into the sensing chamber.

2. A pressure sensor as defined in claim 1 wherein the length of the port is no more than about 2½ times the transverse dimension at said juncture.

3. A pressure sensor as defined in claim 1 wherein said port has a radiused edge at the juncture of the port and the conical surface of the main body.

4. A pressure sensor comprising:
   a main body having an inlet connected to a source of liquid under pressure, an outlet, a passage extending through the main body from the inlet to the outlet so that liquid can flow through the passage;
   a flexible diaphragm confronting a conical surface of the main body coupled to the main body to at least partially define a sensing chamber;
   said main body having a port extending from said passage to said chamber to provide communication between the liquid under pressure in the passage and the sensing chamber; and
   said port at the juncture of the port and the passage having a transverse cross section with at least one dimension which is no greater than about 0.060 inch and having a sharp edge with essentially no radius at said juncture.

5. A pressure sensor as defined in claim 4 wherein said one dimension of said port is no less than about 0.020 inch.

6. A pressure sensor as defined in claim 4 wherein said port is generally circular in said transverse cross section.

7. A pressure sensor as defined in claim 6 wherein said one dimension is no less than about 0.030 inch.

8. A pressure sensor as defined in claim 4 wherein said port is generally rectangular in said transverse cross section.

9. A pressure sensor as defined in claim 8 wherein the rectangular transverse cross section has length and width dimensions and each of said length and width dimensions is no less than about 0.030 inch.

10. A pressure sensor as defined in claim 4 wherein the length of the port is no more than about 0.150 inch.

11. A pressure sensor as defined in claim 4 wherein the port has a radiused edge at the juncture of the port and the conical surface of the main body.

12. A pressure sensor as defined in claim 5 wherein said port has a lesser cross-sectional area at the juncture of the port and the passage than the cross-sectional area of the passage.

13. A pressure sensor as defined in claim 4 wherein said main body is constructed of a molded plastic material and has a lug integral therewith partly defining a slot for use in coupling the main body to a supporting structure.

14. A pressure sensor as defined in claim 4 including a frame having an opening, a compressible tube extending across said opening and means for mounting the main body on the frame.

15. A system for administering a parenteral liquid to a patient comprising:
    conduit means connectable to a source of parenteral liquid and extending to a patient for administering the parenteral liquid to the patient, said parenteral liquid being subject to having bubbles therein;
    a pressure sensor including a main body having an inlet and an outlet coupled to said conduit means and a passage extending through the main body from the inlet to the outlet so that liquid can flow through the passage;
    said pressure sensor including a flexible diaphragm coupled to the main body and confronting a conical surface on the main body for defining a sensing chamber and a port defined in the main body extending from said passage to said sensing chamber to provide communication between liquid under pressure in the passage and the sensing chamber; and
    said port at the juncture of the port and the passage, having a transverse cross section with at least one dimension which is sufficiently small to enable surface tension to substantially exclude the bubbles in the liquid from passing through the port into the sensing chamber, said port having a sharp edge with essentially no radius at said juncture which further serves to exclude bubbles in the liquid from passing through the port into the sensing chamber.

* * * * *

UNITED STATES PATENT AND TRADEMARK OFFICE
CERTIFICATE OF CORRECTION

PATENT NO. : 4,795,440

DATED : January 3, 1989

INVENTOR(S) : Joe W. Young, Michael V. North and Kenneth W. Rake

It is certified that error appears in the above-identified patent and that said Letters Patent is hereby corrected as shown below:

IN THE SPECIFICATION:

Column 2, line 68, after the word "pressure" insert --sensor.--

Column 4, line 19, delete "9" and insert --59--.

Signed and Sealed this

Eighth Day of August, 1989

Attest:

DONALD J. QUIGG

Attesting Officer

Commissioner of Patents and Trademarks